US006850876B1

(12) United States Patent
Lam et al.

(10) Patent No.: US 6,850,876 B1
(45) Date of Patent: Feb. 1, 2005

(54) CELL BASED BINNING METHODS AND CELL COVERAGE SYSTEM FOR MOLECULE SELECTION

(75) Inventors: Raymond L. H. Lam, Mississauga (CA); William J. Welch, Waterloo (CA); Sidney Stanley Young, Raleigh, NC (US)

(73) Assignee: Smithkline Beecham Corporation, Philadelphia, PA (US)

( * ) Notice: Subject to any disclaimer, the term of this patent is extended or adjusted under 35 U.S.C. 154(b) by 0 days.

(21) Appl. No.: 09/564,210

(22) Filed: May 4, 2000

Related U.S. Application Data

(60) Provisional application No. 60/132,516, filed on May 4, 1999.

(51) Int. Cl.[7] .............................. G06G 7/48; G06G 7/58; G06F 17/10
(52) U.S. Cl. ............................... 703/11; 703/2; 702/19; 702/22; 702/27; 435/194; 435/7.2
(58) Field of Search ............................... 703/2; 702/22, 702/27

(56) References Cited

U.S. PATENT DOCUMENTS

| | | | | |
|---|---|---|---|---|
| 5,854,992 | A | * 12/1998 | Shakhnovich et al. | ......... 702/27 |
| 6,162,627 | A | * 12/2000 | Inouye et al. | ................ 435/194 |
| 6,182,016 | B1 | * 1/2001 | Liang et al. | ................... 702/22 |
| 6,185,506 | B1 | * 2/2001 | Cramer et al. | ................. 702/19 |
| 6,240,374 | B1 | * 5/2001 | Cramer et al. | ................. 703/11 |
| 6,538,022 | B1 | * 3/2003 | Pollesello et al. | .......... 514/457 |
| 2002/0009756 | A1 | * 1/2002 | Mandell et al. | .............. 435/7.2 |
| 2002/0107359 | A1 | * 8/2002 | Hogarth et al. | ............. 530/350 |

FOREIGN PATENT DOCUMENTS

| US | WO 99/06839 | * 2/1999 | .......... G01N/33/68 |
|---|---|---|---|
| US | WO 00/67165 | * 9/2000 | ........... G06F/17/50 |

OTHER PUBLICATIONS

"Chemistry Space Metrics in Diversity Analysis, Library Design, and Compound Selection", P. R. Menard, Journal of Chemical Information and Computer Sciences, pp. 1204–1213, Jun. 1998.*
"Experimental Designs for Selecting Molecules from Large Chemical Databases", R.E. Higgs, Journal of Chemical Information and Computer Sciences, pp. 861–869, Sep. 1997.*
"Computational Analysis of Molecular Diversity for Drug Discovery", M.J. Bayley, University of Sheffield, UK, Apr. 6, 1999.*
"RAPID: Randomized Pharmacophore Identification for Drug Design" P.W. Finn, Computational Geometry 97, pp. 324–333, ACM 1997.*
"Efficient Database Screening fro Rational Drug Design Using Pharmacophore–Constrained Conformational Search", S.M. LaValle, ReComb 99, pp. 250–259, ACM Apr. 1999.*

(List continued on next page.)

*Primary Examiner*—Jean R. Homere
*Assistant Examiner*—Fred Ferris
(74) *Attorney, Agent, or Firm*—Michael M. Conger

(57) ABSTRACT

A cell-based binning method ("Data Driven" binning method) allows the inclusion of all molecules, generates a high percentage of occupied cells, and provides adequate division of the molecules in the low-dimensional subspaces (typically all one-dimension (1-D), two-dimension (2-D), and three-dimension (3-D) subspaces). A chemical space coverage criterion ("Uniform Cell Coverage (UCC)" criterion) measures the uniformity of coverage of the molecules selected. A fast exchange design algorithm ("fast exchange UCC" algorithm) that minimizes the number of searches of the candidate points while maximizing the number of exchanges during each pass through the candidate points. This method is many times faster than previous exchange algorithms and generates designs with good coverage properties.

16 Claims, 11 Drawing Sheets

OTHER PUBLICATIONS

"Molecular Diversity in chemical databases: Comparision Medicinal Chemistry Knowledge Bases and Databases of Commercially Available Components", D.J. Cummings, Journal of Chemical Information and Computer Sciences, pp. 750–763 Apr. 1996.*

Burden, "Molecular identification number for substructure searches," *J. Chem. Inf. Comput. Sci.* 29:225–227 (1989).

Doehlert, "Uniform cell designs," *Applied Statistics* 19:231–239 (1970).

Johnson et al., "Minimax and maximin distance designs," *Journal of Statistical Planning and Inference* 26:131–148 (1990).

Kennard et al., "Computer aided design of experiments," *Technometrics* 11:137–148 (1969).

McFarland et al., "On the significance of clusters in the graphical display of structure–activity data," *J. Med. Chem.* :505–514 (1986).

McKay et al., "A comparison of three methods for selecting values of input variables in the analysis of output from a computer code,"*Technometrics* 21:239–245 (1979).

Morris et al., "Bayesian design and analysis of computer experiments: use of derivatives in surface prediction," *Technometrics* 35:243–255 (1993).

Morris et al., "Exploratory designs for computational experiments," *Journal of Statistical Planning and Inference* 43:381–402 (1995).

Pearlman et al., "Novel software tools for chemical diversity", *Perspectives in Drug Discovery and Design* 9–11:339–353 (Jan. 1998).

Schnur, "Design and diversity analysis of large combinatorial libraries using cell–based methods", *Journal of Chemical Information and Computer Sciences* 39:1 36–45 (Jan.–Feb. 1999).

Young et al., "Random versus rational—which is better for general compound screening?," *Network Science* www.netsci.org/science/screening/feature09.html (1996).

Zemroch, "Cluster analysis as an experimental design generator, with application to gasoline blending experiments," *Technometrics* 28:39–49 (1986).

Jones–Hertzog, Deborah K., et al., "Use of recursive partitioning in the sequential screening of G–protein–coupled receptors", *J. Pharmacol Toxicol*, 42, 1999, pp. 207–215.

* cited by examiner

⇓ =LWY DESIGN

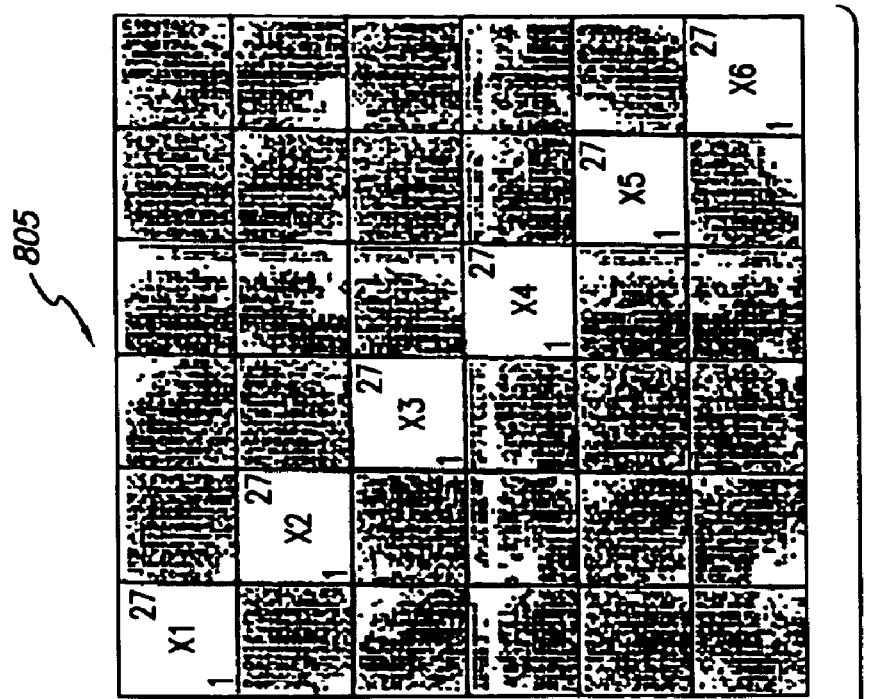
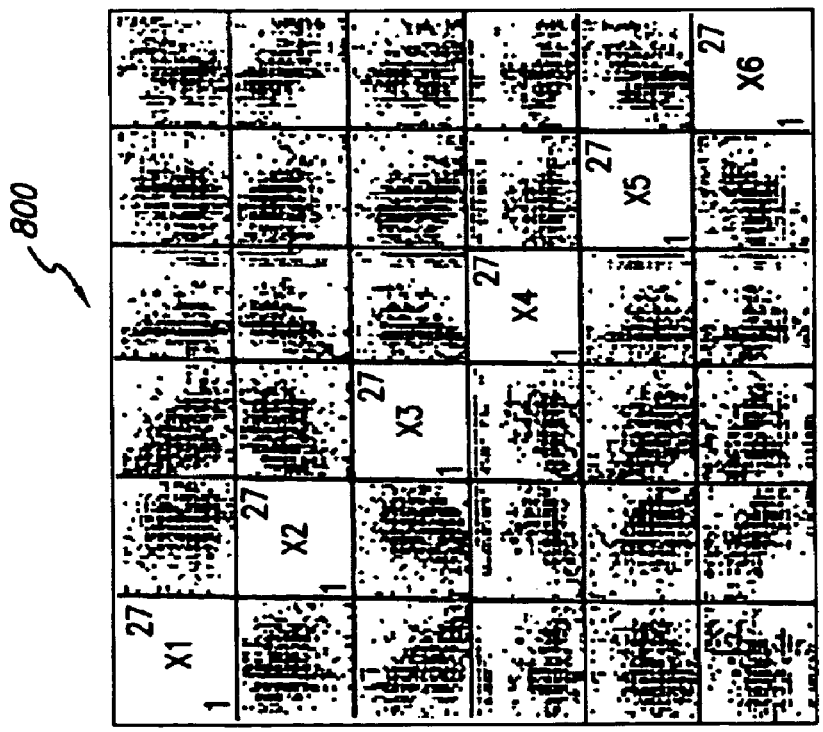
FIG. 8

CELL BASED BINNING METHODS AND CELL COVERAGE SYSTEM FOR MOLECULE SELECTION

CROSS-REFERENCE TO RELATED APPLICATION

This application claims priority from U.S. Provisional Application No. 60/132,516, entitled "CELL BASED BINNING METHODS AND CELL COVERAGE SYSTEM FOR MOLECULE SELECTION", by Raymond L. H. Lam, William J. Welch and S. Stanley Young, filed on May 4, 1999, which U.S. Provisional Application No. 60/132,516 is fully incorporated herein by reference.

FIELD OF INVENTION

The present invention is related to drug research technology. More particularly, the present invention provides a system and method for enhancing successful discovery of drugs using high throughput biological screening technology by providing a representative set of compounds to screen. This provides a general method for selecting representative objects.

BACKGROUND OF THE INVENTION

The use of robotics and miniaturization is now allowing researchers to quickly screen thousands of compounds for biological activity. Combinatorial chemistry provides the logistics of mass production of compounds and a wide range of molecular diversity for drug discovery. The automation of biological assays, High Throughput Screening (HTS), allows for investigation of thousands of compounds against biological targets per week. While this brute-force approach to lead generation certainly has its place in the field of drug discovery, it is not practical to adopt HTS for every new target of potential biological importance, given the size of today's chemical libraries (e.g., hundreds of thousands to millions of compounds).

Various molecular descriptors (explanatory variables) can be readily computed to describe the chemical properties of every molecule in the database. When there is no prior model relating biological response to these descriptors, the generally accepted procedure is to screen (test) a diverse subset of the overall database, and then examine further compounds that are structurally similar to any promising leads. Measures of "diversity" and "similarity" are based on the numerical descriptors. The assumption here is that similar objects are more likely to have similar biological responses. Thus, if an initial subset is to be selected, the subset should "fill" or "cover" the numerical space in some sense. Ideally, selected objects should be as dissimilar as possible and any candidate not selected should be near a molecule in the experimental design.

To measure the "coverage" of a descriptor space, the space is divided into cells. A good experimental design will ideally have at least one molecule in every cell. When this condition is met, the space is said to be covered. In a conventional cell-based method, the range for each of the k descriptors is subdivided into m bins of equal size, yielding $m^k$ cells. With even moderate values of m and k, a huge number of cells are generated, most of which are empty even for the candidate set of all molecules in the database. Any subset selected has even poorer coverage of the cells, making comparison of potential experimental designs difficult.

FIG. 1 shows the univariate and pairwise plots (100 and 105) of the six descriptors for the NCI candidate molecules (described later), with the distributions of the NCI molecules in one-dimension (1-D) and two-dimensions (2-D) projections for all 6 descriptors. It is clear that much of the space is empty. Either the collection is missing chemicals or it is not possible to make compounds with certain combinations of descriptors. In more than two dimensions, this problem will be even worse. Consequently, to deal with a problem of practical importance, P. R. Menard et al., "Chemistry Space Metrics in Diversity Analysis, Library Design, and Compound Selection," Journal of Chemical Information and Computer Sciences, 38, 1204–1213, (1998), restricted the number of descriptors to 3 to 6 and the number of bins per descriptor to 4 to 7 and excluded a large number of candidate points by treating them as outlying observations. Even with these restrictions, over 80% of cells were empty in an example that they presented with $6^6$ cells.

A discussion is now made of the various existing methods for selecting an experimental design to cover a space of explanatory variables and the deficiencies in these existing methods. The most common designs for selecting diverse molecules are random designs, distance designs, and cell-based binning designs.

The simplest designs are based on random sampling. In fact, most new leads have been discovered through random screening, in which large numbers of compounds are tested for a specific biological activity, and the active compounds are then selected for optimization. S. S. Young et al., "Random Versus Rational—Which is Better for General Compound Screening?", Network Science, www.netsci.org/Science/Screening/feature09.html (1996), used a constant radius hypersphere around each randomly selected compound to measure the coverage of the descriptor space. They concluded that, unless a very large number of compounds are used to fill space, randomly selected compounds will cover as much space as carefully selected compounds. On the other hand, if the important dimensions for a particular problem are identified, and if a focused set of compounds is desired, then rational selection should be more effective than random designs.

There are three main types of distance based designs for selecting molecules from chemical databases. R. E. Higgs et al., "Experimental Designs for Selecting Molecules from Large Chemical Databases," Journal of Chemical Information and Computer Sciences, 37, 861–870 (1997), refer to these as "Edge", "Spread" and "Coverage" designs. These methods first define a descriptor distance metric (e.g., Euclidean or Manhattan distance) to measure the similarities or dissimilarities of the molecules, and then find the optimal coverage of the space based on some distance criterion. Edge (D-optimal) designs identify molecules at the edge of the descriptor space that produce minimum variance estimators for parameters in a regression model that is linear in the descriptors (explanatory variables). Spread designs (see, e.g., R. W. Kennard et al., "Computer Aided Design of Experiments," Technometrics 11, 137–148 (1969)) identify a subset of molecules that are maximally dissimilar with respect to each other. Coverage designs (see, e.g., P. J. Zemroch, "Cluster Analysis as an Experimental Design Generator, With Application to Gasoline Blending Experiments," Technometrics 28, 39–49 (1986)) select a subset of molecules that are maximally similar to the candidate set of molecules. The following references provide more detailed descriptions of these designs: R. E. Higgs et al., "Experimental Designs for Selecting Molecules from Large Chemical Databases," Journal of Chemical Information and Computer Sciences, 37, 861–870 (1997); M. E. Johnson et al., "Minimax and Maximin Distance Designs,"

Journal of Statistical Planning and Inference 26, 131–148 (1990); and R. Tobias, SAS QC Software. Volume 1: Usage and Reference, SAS Institute Inc., Cary, N.C., 657–728 (1995).

There are three problems with distance-based designs. First, in general these designs try to find a subset with optimal coverage of the entire descriptor space but pay little attention to the coverage in lower-dimensional subspaces. The low-dimensional coverage (i.e., 1-D, 2-D and 3-D) can be quite poor. The following references addressed this tissue by incorporating 1-D coverage into their spread designs: M. D. Morris et al., "Bayesian Design and Analysis of Computer Experiments: Use of Derivatives in Surface Prediction," Technometrics 35, 243–255 (1993); and M. D. Morris et al., "Exploratory Designs for Computational experiments," Journal of Statistical Planning and Inference, 43, 381–402 (1995). Secondly, descriptors that are unrelated to target activity can have a significant impact on the distribution of the molecules in the space, and can make the "optimality" of a design irrelevant. Without proper selection of descriptors, these optimal designs are not expected to improve the quality of rational sampling over that of random sampling. Thirdly, the presence of relatively few outlying observations can have significant impact on these designs. Very often this requires removal of many outlying molecules to come to a sensible design.

In the conventional cell-based method, each of the k numerical descriptors is subdivided into m bins of equal size, yielding $m^k$ cells or hypercubes, and the experimental design chooses at least one molecule from every cell. This method is attractive because it is easy to divide the descriptor space into cells and allocating even a very large dataset to these cells is straightforward. Missing diversity (i.e., empty cells) can easily be identified. The following references disclose cell-based binning methods to compare the relative diversity of molecular databases and to select diverse subsets of molecules: D. J. Cummins et al., "Molecular Diversity in Chemical Databases: Comparison of Medicinal Chemistry Knowledge Bases and Databases of Commercially Available Compounds," Journal of Chemical Information and Computer Sciences, 36, 750–763 (1996); and P. R. Menard et al., "Chemistry Space Metrics in Diversity Analysis, Library Design, and Compound Selection," Journal of Chemical Information and Computer Sciences, 38, 1204–1213 (1998). A problem with many existing cell-based binning methods is that they generate too many cells and many of the cells are empty. Even when k and m are relatively small, the number of empty cells is often more than the number of nonempty cells for chemistry problems. To reduce the number of empty cells, Cummins et al. (1996) and Menard et al. (1998) restricted the number of descriptors and the number of bins per descriptor. They also excluded many outlying candidate points. Even with these compromises, they reported a large proportion of empty cells. Indeed, a very low cell occupancy is expected by Menard et al. (1998)—they recommended a targeted occupancy of 12–15%.

Two popular space-filling designs, currently only applied to more regular sampling spaces, are Latin hypercube designs (see, e.g., M. D. McKay et al., "A Comparison of Three Methods for Selecting Values of Input Variables in the Analysis of Output from a Computer Code," Technometrics 21, 239–245 (1979)) and uniform shell designs (see, e.g., D. H. Doehlert, "Uniform Shell Designs," Applied Statistics, 19, 231–239 (1970)). Latin hypercubes have excellent 1-D coverage and are very popular in experiments with computer models. The main problem in applying these methods to compound selection is that for chemical compounds only certain combinations of descriptor values exist.

Some of the other problems related to design and analysis of molecular data include:

1. The model is vague. In many drug design problems, it is not clear which model is appropriate to relate biological response to molecular properties beyond the assertion that similar objects are more likely to respond similarly. Thus if a collection of chemical objects are described numerically and if a subset is to be selected, then the subset should "fill" the numerical space in some sense—selected objects should be as dissimilar as possible or any candidate not selected should be near a selected object.

2. There is more than one response. Several biological screenings, each designed to detect a specific biological activity, may be in operation within the research division of a pharmaceutical company at any given time. It is hoped that the collective output of these screens will provide enough leads to contribute to the discovery process in a meaningful way.

3. The samples to be chosen from are often a collection of restricted sampling points and their descriptor values are dependent. A standard experimental design procedure assumes that the descriptor space can be represented as a region bounded by a k-dimensional hypercube with any points in the cube being a candidate point. The standard design is not possible for compound selection problems because, even though the space is continuous, the possible molecules are discrete. It is not possible to place a compound at certain positions in the space. One is restricted to the compounds that one has or can make.

4. The number of candidate points ($N_c$) and the number of design points ($n_d$) are large. The number of possible combinations of the samples to be chosen from is so large that it becomes computationally impossible to consider every possible combination in the experimental design—it may take days or weeks or even months to compare every combination. In theory, to identify the optimal design, one needs to examine all possible subsets of size $n_d$ from the $N_c$ candidate points, thus performing $N_c$-chose-$n_d$ subset evaluations. In practice, the magnitudes of $N_c$ and $n_d$ prohibit a full scale optimization. For example, even to choose a small design of 100 points from a very small candidate set of 1000 molecules, there are $6.4 \times 10^{139}$ possible subsets. For moderate or large datasets, search algorithms are usually applied to find a very good design, as it is impossible to find the globally best design.

5. The number of descriptors can be very large. Tens to hundreds to thousands of molecule descriptors are possible. This implies a high dimensional problem.

Thus, what is needed is a fast method to select representative objects while providing optimal (or near optimal) space coverage.

SUMMARY OF INVENTION

The present invention provides an efficient and effective system and method for enhancing successful discovery of drugs using high throughput biological screening technology by providing a representative set of compounds to screen.

Embodiments in accordance with the present invention include the following:

1. A cell-based binning method (hereinafter referred to as the "Data Driven" binning method) allows the inclusion of all molecules, generates a high percentage of occupied cells for the candidate set, and provides adequate selection of the molecules to cover the low-dimensional subspaces (typically all one-dimension (1-D), two-dimension (2-D), and three-dimension (3-D) subspaces).

2. A chemical space coverage criterion (hereinafter referred to as the "Uniform Cell Coverage (UCC)" criterion) measures the uniformity of coverage of the molecules selected.

3. A fast exchange design algorithm (hereinafter referred to as the "fast exchange UCC" algorithm) that minimizes the number of searches of the candidate points and points from the provisional design for exchange, while maximizing the number of exchanges during each pass through the candidate points. This method is many times faster than previous exchange algorithms and generates designs (representative sets) with good low dimensional coverage properties.

These methods will be described in the detailed description. While this invention will be described with reference to drug research, the methods disclosed herein are also adaptable to many other applications, e.g., selection of patients for clinical trials.

For convenience, the terms "UCC" and "LWY" designs are used interchangeably.

BRIEF DESCRIPTION OF THE DRAWINGS

FIG. 8 illustrates diagrams comparing 2-D coverage between the random design and the UCC design;

DETAILED DESCRIPTION

Figure 1:
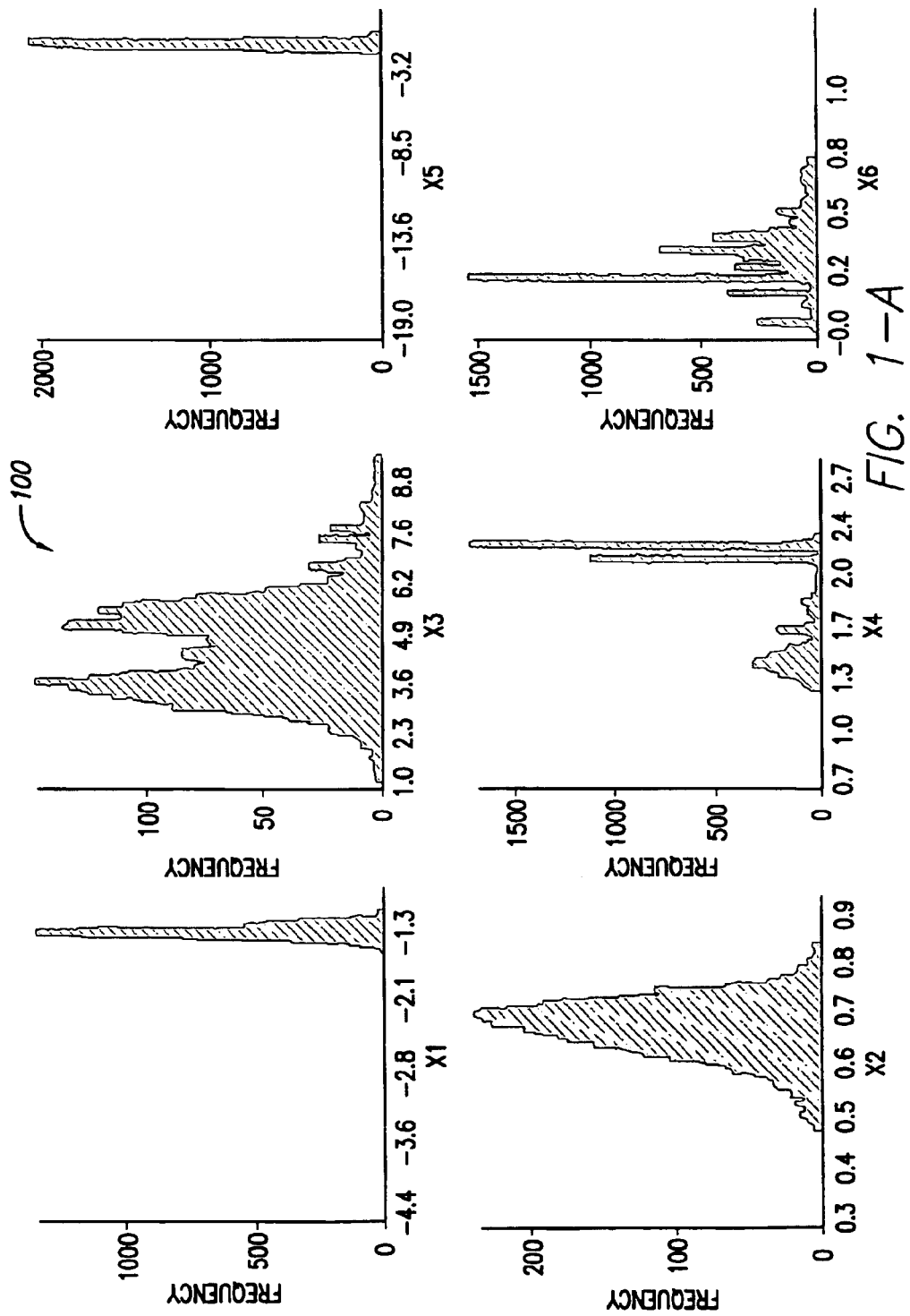
FIG. 1 illustrates diagrams of univariate and pairwise plots of the six descriptors for the NCI molecules.

Those of ordinary skill in the art will realize that the following description of the preferred embodiments is illustrative only and not in any way limiting. Other embodiments of the invention will readily suggest themselves to those skilled in the art.

Terminology Used and Notation

The following terms and terminology will be used in the description. A brief definition follows each of which is meant to instruct, but not limit, the use of the term as provided.

A Candidate Point is an object that can be tested, for example, a molecule or a patient. A "good" candidate point is one that has different characteristics from those that have already been selected. For distance-based designs, the "best" candidate point is one that is maximally dissimilar to those that have been selected; for cell-based designs, the "best" candidate point is the one that fills the most unfilled low-D cells.

An optimal design or a locally optimal design: if exchanging the "best" candidate and design points yields no further improvement to the design.

Molecule, compound and structure: For simplicity and brevity, the terms "molecule", "compound" and "structure" are used interchangeably. Technically, a compound is a chemical substance with two or more elements. A molecule is the simplest structural unit that displays the characteristics physical and chemical properties of a compound. A structure is the graphical presentation of the bonds and atoms of a compound. In drug discovery, a compound is considered a chemical substance not yet defined, while a molecule is a defined compound. Graphically, a molecule is referred to a chemical structure.

NCI molecules: Molecules from a National Cancer Institute (NCI) chemical database, with the NCI database having over 29,000 molecules and having data in the public domain. The NCI chemical database can be obtained from, for example, the following web site: http://dtp.nci.nih.gov/docs/aids/aids_data.html. In May 1999, there were 32,110 compounds in the NCI DTP AIDS antiviral screen database. Some of these molecules were removed as their descriptors could not be computed, leaving 29,217 unique molecules. They are described by six continuous variables (descriptors), which measure molecular bonding patterns, and atomic properties such as surface area, charge, hydrogen-bond donor and acceptor ability. The descriptors, called BCUT values, are based on the work by F. R. Burden, "Molecular Identification Number for Substructure Searches," Journal of Chemical Information and Computer Sciences, 29, 225–227 (1989). It was found that structurally similar compounds usually have very similar-BCUT values.

Core98 molecules: Molecules from a proprietary molecular database called Core98. There are 23,056 unique molecules in the Core98 database, and these are described by six BCUT continuous variables.

In general, denote the k continuous descriptors by $x_1$, $x_2, \ldots, x_k$, and let $X_c$ be a candidate set with $N_c$ candidate points. The objective is to choose a representative set of $n_d$ design points, $X_d$, to cover the descriptor space occupied by the candidate set.

Within the full k-dimensional descriptor space, a p-dimensional (p-D) subspace is defined by p of the k descriptors ($1 \leq p \leq k$). For convenience, these subspaces will be referred to as Xi for 1-D subspaces, Xij for 2-D subspaces, and Xij1 for 3-D subspaces. For example, X1 is a 1-D subspace defined by $x_1$, and X12 is a 2-D subspace formed by $x_1$ and $x_2$.

Cell-Based Approach

We use a number of techniques to keep the cells small, yet limit their number, and to ensure that relatively few cells are empty in the candidate set. First, we focus attention on low-dimensional subspaces, typically all 1-D, 2-D, and 3-D subspaces. By considering no more than three variables at a time, fewer cells are required to represent a subspace. Selecting a design with good coverage of all low-dimensional subspaces is analogous to a two-level fractional factorial design of Resolution IV. Such a design is a complete factorial for any subset of three or fewer variables (see, e.g., Box et al., Statistics for Experimenters, New York: Wiley (1978) p. 388) and can estimate all interaction effects if only three factors are found to be important. Secondly, we keep the number of cells constant over all subspaces, avoiding the exponential increase with dimension. Thirdly, to avoid empty cells caused by the sparsity of molecules towards the limits of a descriptor's range, we adopt a data-driven hybrid binning method that makes bins larger towards the extremes.

A descriptor bin is a segment of a descriptor range. Cells are formed by combining descriptor bins. Larger descriptor bins are used for higher-dimensional subspaces in order to keep the number of cells in each subspace constant.

For example, for any 1-D subspace a single descriptor's range could be divided into 729 distinct (or disjoint) intervals to form 729 descriptor bins. (It will be explained below why 729 is a convenient number). As only one descriptor is involved for a 1-D subspace, the 729 bins immediately become the 729 cells for the subspace. For a 2-D subspace, each of the two descriptor ranges could be divided into 27 bins. The 2-D subspace will have 27×27=729 cells formed by combining the 1-D bins. Similarly, for any 3-D subspace, 9 bins for each descriptor range would give 9×9×9=729 cells.

The number 729 is convenient as it has an integer square and cube root. In general, there would typically be m cells per subspace. For 1-D, 2-D, and 3-D subspaces, there would typically be $m$, $m^{1/2}$, and $m^{1/3}$ bins per descriptor, respectively. Thus, convenient values of m are, for example, $2^{2 \times 3}=64$, $3^{2 \times 3}=729$ and $4^{2 \times 3}=4096$, $5^{2 \times 3}=15625$, etc.

Figure 2:
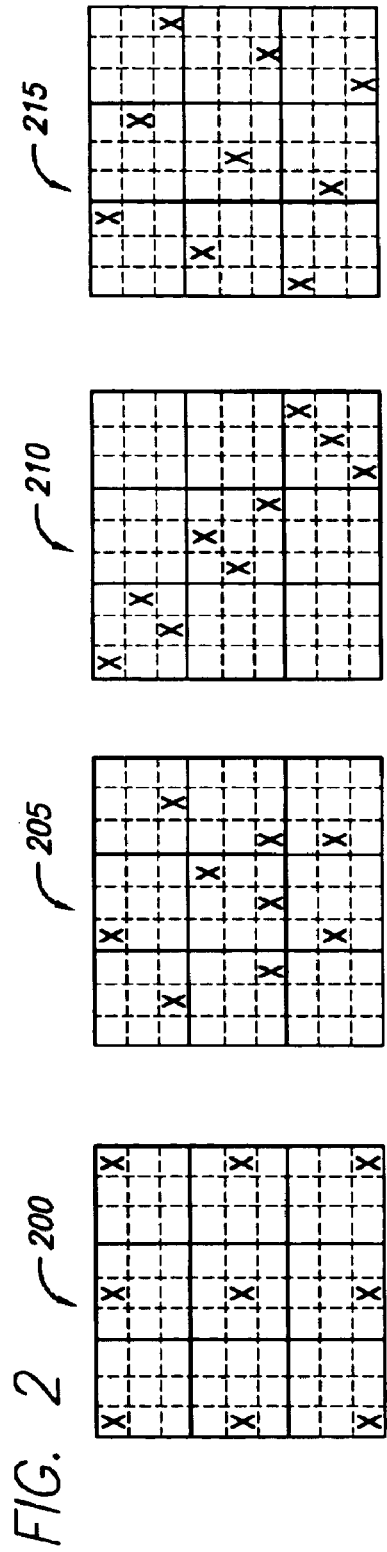
FIG. 2 illustrates block diagrams of equal number of cells in 1-D and 2-D subspaces and four types of space filling designs, with nine 1-D cells in the 1-D subspaces and nine 2-D cells (3 by 3) in the 2-D subspaces.

For example, suppose we have two descriptors and we want to select nine design points. FIG. 2 illustrates how the 1-D and 2-subspaces can each be divided into nine cells. Each of the two 1-D subspaces for descriptors 1 and 2 are divided into nine 1-D cells and the 2-D subspace is divided into nine 2-D cells (i.e., 3 by 3). Therefore, there are nine 1-D cells in each 1-D subspace and nine 2-D cells in the 2-D subspace. To illustrate the binning method, four example designs are included in FIG. 2 with each of the nine design points denoted by "X". The max-min design (200), representing both the Edge and Spread designs, gives very poor 1-D projections (i.e., it covers only three of the nine 1-D cells in each dimension). The random design (205) gives better 1-D projections but still does not cover all nine cells in each 1-D subspace and all nine cells in the 2-D subspace. The "good 1-D projections" design (210) covers all nine cells in each 1-D subspace but covers only three of the 2-D cells. Finally, the "good 1-D/2-D projections" design (215) gives good coverage in all three subspaces: Every cell is occupied.

With k descriptors, there are $$\binom{k}{1} + \binom{k}{2} + \binom{k}{3} = \frac{5}{6}k + \frac{1}{6}k^3$$

1-D, 2-D, and 3-D subspaces in total. When k=3, for example, there are 7 subspaces: X1, X2, X3, X12, X13, X23 and X123. When k=6, there are 41 subspaces and when k=10, there are 175 subspaces. For larger k, it might be necessary for computational reasons to reduce the number of subspaces by focusing on, for example, only 1-D and 2-D subspaces.

Including subspaces of 4-D and higher will usually not be practical. Chemists generally believe that two molecules must have fairly close values of all critical descriptors for similar biological activity (see, e.g., J. W. McFarland et al., "On the Significance of Clusters in the Graphical Display of Structure-Activity Data," Journal of Medicinal Chemistry, 29, 505–514 (1986)). This indicates that bins have to be small if one molecule from a bin is to represent the rest. Yet, even with 10 bins per dimension, which is probably too few, there are 10,000 cells per 4-D subspace. Clearly, we would need to choose at least this many molecules if the experimental design is to cover every cell. Thus, it is not possible to give dense coverage of a 4-D subspace with a modest subset of molecules. For analysis, this implies that interaction effects are hopefully limited to no more than three factors.

How big should m be? Even with the data-driven binning method described next, there will be some cells with no molecules. The proportion of empty cells, which varies from subspace to subspace, will tend to increase with m. In addition, if $n_d$ design points are to be selected, $n_d$ nonempty cells per subspace are typically chosen, so that a good space-filling design can cover distinct nonempty cells. These two considerations suggest that m should be approximately equal to $n_d$ or a little larger.

In an embodiment of the invention, we use a hybrid of two simple-to-implement methods, Equal Width (EW) and Equal Frequency (EF), to construct bins. The EW method simply divides a descriptor's range into equal-width intervals. Alternatively, EF bins have cut-points chosen to make the frequency of candidate points approximately equal in each bin. The present invention provides a data-driven, hybrid method that combines the best features of EW and EF bins.

In regions where there is a reasonable density of descriptor values, EW bins are compelling. When a molecule is chosen to represent a bin (and hence a cell), it is the size of the bin that determines the quality of coverage in the descriptor space, nor the number of molecules in a bin. Another way of looking at this is that EF bins are very small where there is a high density of candidate molecules. Such regions will be over-represented in an experimental design, to the detriment of coverage in regions where candidates are sparse and bins are wide.

On the other hand, outlying or extreme descriptor values may inflate a descriptor's range, making many EW bins empty towards the extremes. This problem is compounded in multiple dimensions: Unless every bin forming a cell is nonempty, the cell is empty. To avoid this, extreme candidates are sometimes removed from consideration (see, e.g., Cummins et al. (1996) and Menard et al., (1998)). By definition, the EF method has candidate points in every 1-D bin and hence none are empty. Empty cells in 2-D or 3-D subspaces can still arise, but EF bins will tend to have fewer empty cells.

To combine the best features of EW and EF bins, we use a data-driven, hybrid method. EF bins are constructed for the extreme values. For example, the first percent of a descriptor's values can be placed in one bin, with a similar bin for the last one percent. EW bins are then used between these extreme bins. Thus, EW bins predominate, while the EF method for the extreme values avoids empty bins.

Figure 3:
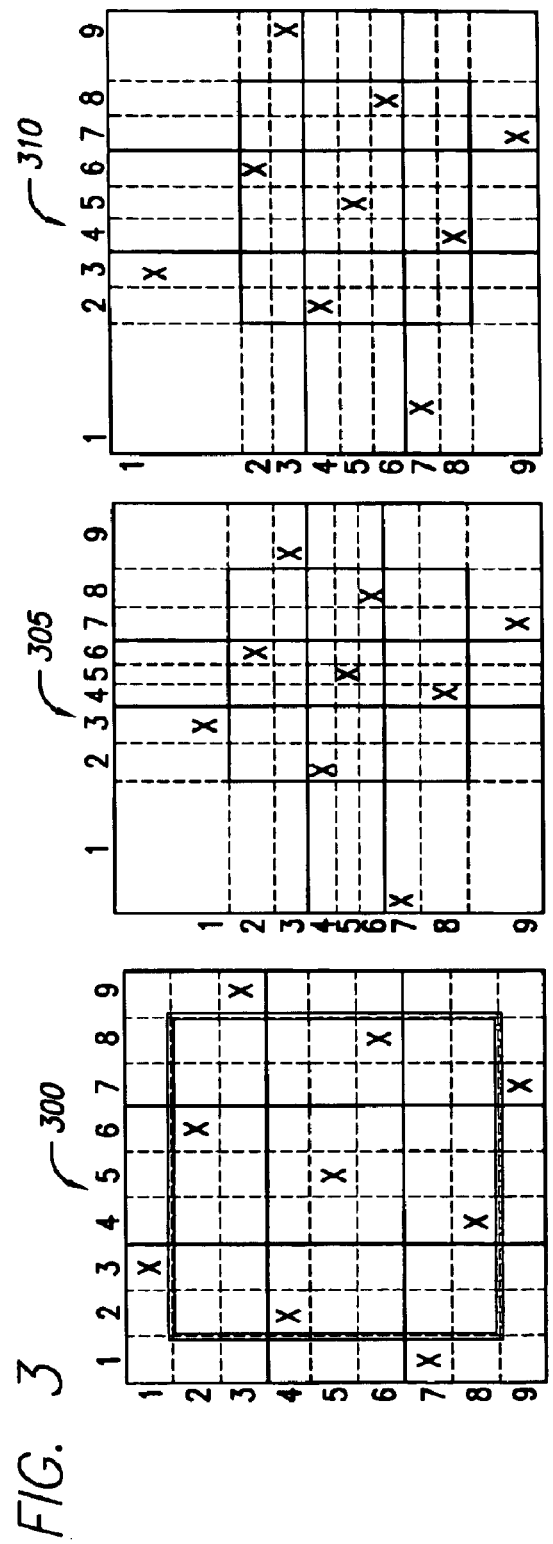
FIG. 3 illustrates block diagrams of an Equal Width (EW) bin, an Equal Frequency (EF) bin, and a hybrid bin in accordance with an embodiment of the present invention.
Figure 4:
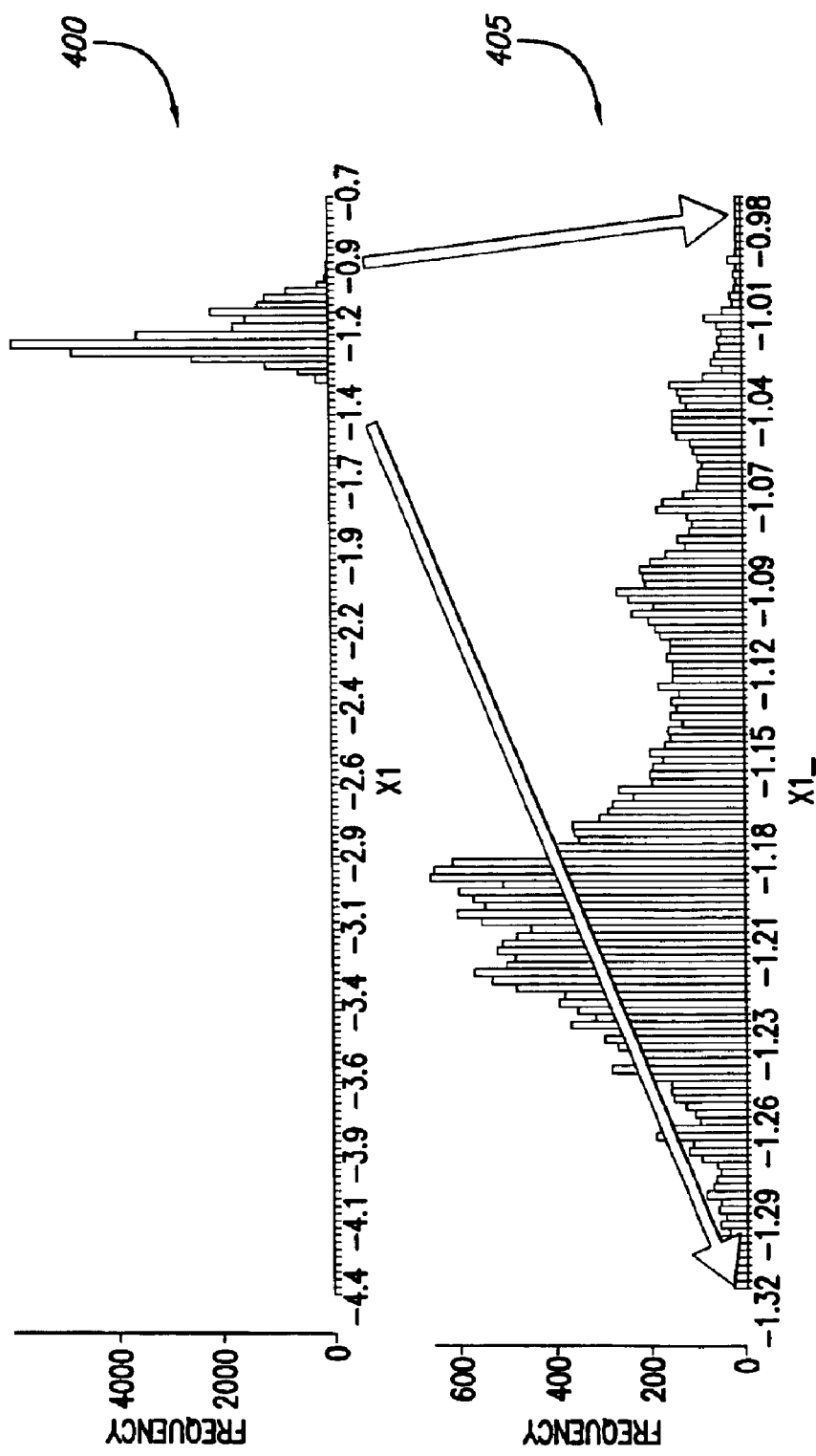
FIG. 4 are charts illustrating applications of the EW bins and the Hybrid bins that lead to, respectively, many empty bins and zero empty bins.

The concept of EF (300) versus EW (305) versus Hybrid (310) bins is illustrated in FIG. 3. The nine design points show how the space may be covered using the various binning approaches. FIG. 4 similarly compares the distribution of molecules into EW (400) or hybrid (405) bins for the X1 subspace of the NCI database. In both cases, 150 bins are used. It is clear that many of the EW bins in the top histogram are empty. In contrast, in the bottom histogram there is one EF bin (the first percentile), 148 EW bins, and then one EF bin (the last percentile), which generates no empty bins.

Criteria for Evaluating Coverage

In a conventional cell-based design, there is one set of cells based on all k descriptors. Simply picking a point from each occupied cell guarantees a good coverage design. However, as mentioned, this can generated too many empty cells. Previously, we defined cells based on low-dimensional subspaces to overcome this problem. With more than one subspace, it is no longer straightforward to select a set of candidate points to give good coverage simultaneously in many subspaces. If, say, one point is chosen from each cell in a particular subspace, these points may be unevenly distributed in other subspaces. We now describe two measures of the quality of coverage; the second measure will be used below (Fast Exchange Algorithm section) as an optimization criterion to drive the numerical search for a good experimental design.

We first need some definitions and notation. Let X denote a set of points (molecules) in the descriptor space; X will typically be the entire set of candidate points, $X_c$, or a trial experimental design, $X_d$. The set X is said to cover cell i in subspace s if at least one of the points falls in that cell. Mathematically, we set up indicator variables $c_{si}(X)$ taking the value 1 if cell i in subspace s is covered and 0 otherwise.

The first experimental design criterion simply computes the percentage of cells that are covered by a design, averaged over all subspaces. Some cells are not covered by the candidate set, $X_c$, and so cannot be covered by any choice of design; these cells are eliminated from consideration when computing the criterion.

In subspace s, the percentage of cells covered by a design $X_d$ is:

$$P_s = \frac{\sum_i c_{si}(X_d)}{\sum_i c_{si}(X_c)} \times 100\% \tag{1}$$

where the summation is over all cells in the subspace. We can then define the average percentage coverage over, for example, all 1-D subspaces as:

$$P_{1\text{-}D} = \frac{\sum_{i \in S_1} P_s}{|S_1|} \tag{2}$$

where $S_1$ is the set of all 1-D subspaces and $|S_1|$ is the number of such subspaces. For 2-D subspaces we define $P_{2\text{-}D}$ analogously, and so on. For example, the average percentage coverage over all 2-D subspaces is:

$$P_{2\text{-}D} = \frac{\sum_{i \in S_2} P_s}{|S_2|} \tag{3}$$

We can them obtain the average percentage cover, P. For example, if 1-D, 2-D, and 3-D subspaces are being considered, the P can be calculated as follows:

$$P = \frac{\left(P_{1\text{-}D} + P_{2\text{-}D} + P_{3\text{-}D}\right)}{3} \tag{4}$$

The average could also be weighted, for example, by giving more weights to 1-D subspaces. One deficiency of this criterion is that it ignores the distribution of design points in the covered cells. For instance, consider two very different space filling designs: one design has two points in each of 50 cells and the other design has 1 point in 49 of these cells and 51 points in the remaining cell. With respect to these 50 cells, the coverage is 100% for both designs, yet we would prefer the first design as the distribution of points is more uniform. Thus the criterion P is modified to select a design that takes the uniformity of coverage into consideration.

Uniform Cell Coverage (UCC)

Suppose design $X_d$ places $n_{si}(X_d)$ points in cell i of subspace s. If the candidate set $X_c$ does not cover this cell (i.e., $c_{si}(X_c)=0$), then $n_{si}(X_d)$ has to be 0. For cells that are covered by $X_c$ (i.e., $c_{si}(X_c)=1$), it is preferred that $n_{si}(X_d)$ counts are approximately 1. Thus, ideally, $n_{si}(X_d)=c_{si}(X_c)$ for every cell. In subspace s, then, a measure of lack of uniformity is:

$$U_s = \sum_i [n_{si}(X_d) - c_d(X_c)]^2 \tag{5}$$

Again, these quantities can be accumulated over subspaces. The total lack of uniformity for 1-D subspaces, for example, is:

$$U_{1\text{-}D} = \frac{\sum_{r \in S_1} U_s}{|S_1|} \tag{6}$$

and $U_{2\text{-}D}$ can be defined analogously, and so on. For example, the total lack of uniformity for 2-D subspaces is:

$$U_{2\text{-}D} = \frac{\sum_{s \in S_x} U_x}{|S_2|} \tag{7}$$

By averaging with weights across, for example, the 1-D, 2-D, and 3-D subspaces, the uniform cell coverage (UCC) criterion can be calculated as U:

$$U = \frac{\left(w_1 U_{1\text{-}D} + w_2 U_{2\text{-}D} + w_3 U_{3\text{-}D}\right)}{w_1 + w_2 + w_3}, \tag{8}$$

where $w_1$, $w_2$, and $w_3$ are weights. In the examples below (Results section), equal weights are used.

Minimizing U in equation (8) discourages uncovered cells in the design and tends to avoid having more than one design point per cell. This is the criterion used by the optimization method in accordance with an embodiment of the present invention.

The indicator variables $c_{si}(X_c)$ in equation (5) provide the target numbers of points per cell in the UCC criterion. With a simple modification to these targets, a generalized UCC is obtained. For example, suppose that we want two design points in each cell. We can set the target for a cell to 0, 1, or 2 if there are no candidate points, one point, or at least two points, respectively. In the examples of this disclosure, we use equation (5) without modification.

Figure 9:
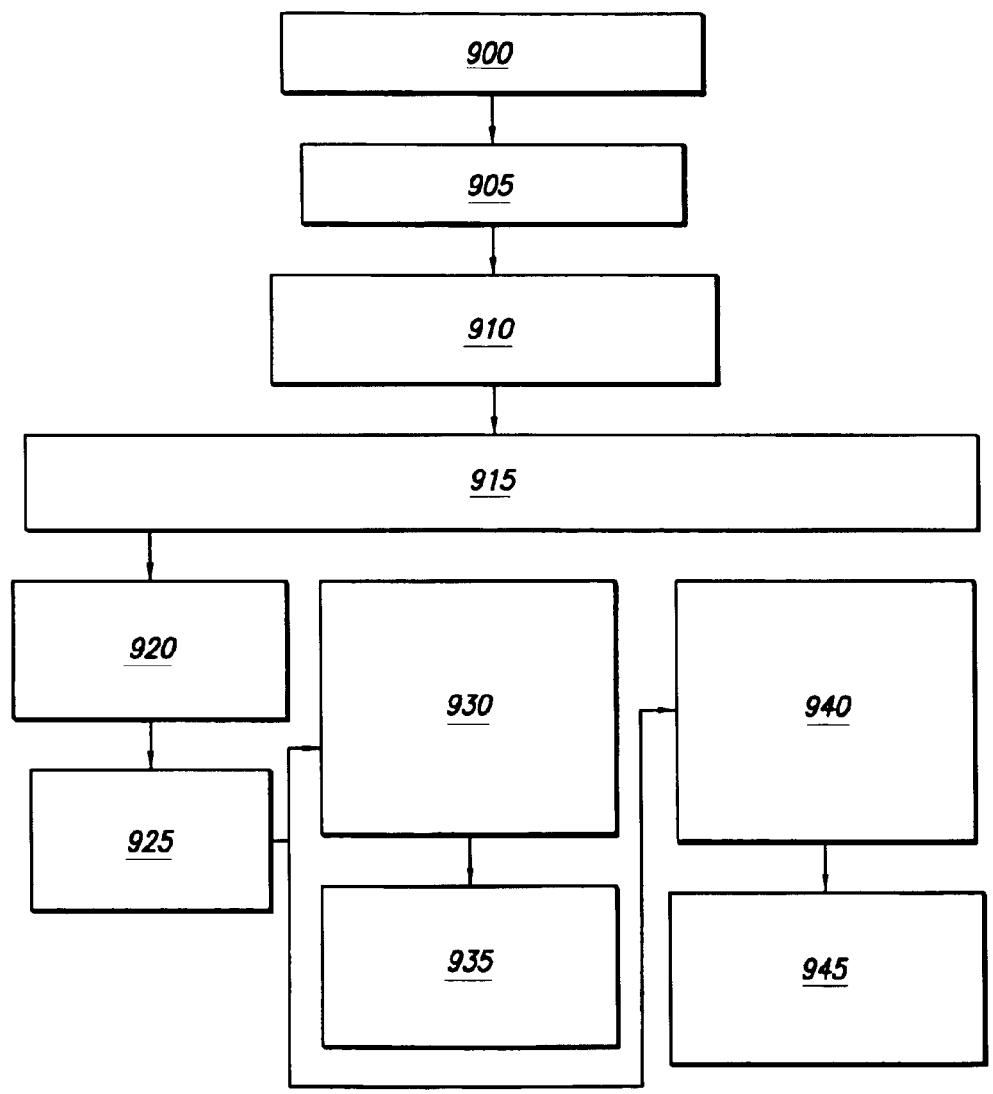
FIG. 9 illustrates a flowchart of a method of dividing low dimensions of a high mathematical space into a finite number of bins.

FIG. 9 illustrates a flowchart of a method of dividing low dimensions of a high mathematical space into a finite number of bins. The process is as follows:

1. Determine the low-D subspaces to be examined (e.g., 1-D/2-D/3-D subspaces) (step 900).
2. Choose the number of cells in a subspace, say m cells per subspace (e.g., m=64, 729 or 4096) (step 905).
3. Decide the number of extreme points to be included in the first and last bins (e.g., 1% of points in each bin) (step 910).
4. Divide each descriptor's range into m, $m^{1/2}$ and $m^{1/3}$ bins for, respectively, 1-D, 2-D and 3-D subspaces (i.e., if dimension=1-D, then divide a descriptor's range into m bins; if dimension=2-D, then divide the range into $m^{1/2}$ bins; if dimension=3-D, then divide the range into $m^{1/3}$ bins) as follows (step 915).
5. For each 1-D subspace, do the following:
   5a. Determine the cut points of the first and last bins for each descriptor, say c1 and c2 (step 920).
   5b. The width of the remaining (m−2) bins are then equal to (c2−c1)/(m−2). The cut point for bin i is equal to c1+(i−1)*(c2−c1)/(m−2), i=2, . . . , m−1. These generate m 1-D hybrid bins and thus m 1-D cells per 1D subspace (step 925).
6. For each 2-D subspace, do the following:
   The first $m^{1/2}$ 1-D bins form the first 2-D bin; the second $m^{1/2}$ 1-D bins form the second 2-D bin, and so on (step 930). These generate $m^{1/2}$ 2-D bins and thus $m^{1/2} \times m^{1/2}$ 2-D cells per 2-D subspace (step 935).
7. For each 3-D subspace, do the following:
   The first $m^{1/3}$ 1-D bins form the first 3-D bin, the second $m^{1/3}$ 1-D bins form the second 3-D bin, and so on (step 940). These generate $m^{1/3}$ 3-D bins and $m^{1/3} \times m^{1/3} \times m^{1/3}$ 3-D cells per 3-D subspace (step 945).

Fast Exchange Algorithm

With conventional cell-based binning, which focuses on the one space of all descriptors, choosing a subset of molecules is straightforward: One or more molecules is randomly sampled from each nonempty cell. This strategy does not work for the UCC criterion above, however. Randomly sampling in the nonempty cells of one subspace might give a poor distribution of molecules in another subspace. Thus, an optimization algorithm is needed; we modify the exchange algorithm as disclosed in H. P. Wynn, "Results in the theory and construction of D-optimal experimental designs," Journal of the Royal Statistical Society B, 34, 133–147 (1972). The adaptations greatly reduce the computational effort, especially when dealing with very large candidate sets.

Wynn's algorithm starts with a random subset of $n_d$ points (an initial design) from the $N_c$ candidates. The optimization criterion is then sequentially improved by a series of exchanges. (Wynn worked with a criterion called D optimality, but we will use UCC.) In each exchange, a point in the candidate set replaces a point in the current design. An exchange is broken down into two steps. First, a point in the candidate list is found to add to the current design. The point added from the candidate list is the one with the best value of the design criterion for the modified design of $n_d+1$ points. Second, a point in the new design of $n_d+1$ points is removed; this point is chosen to give the best criterion value for the new design of $n_d$ points amongst those that are subsets of the $n_d+1$ points available. These exchanges continue until the criterion cannot be improved.

For moderate to large lists of candidate molecules, Wynn's algorithm can be made much faster. Moreover, our algorithm tends to find a better value of the design criterion. We now describe the adaptations.

Identifying Good Candidates for Exchange

Wynn's algorithm is computationally inefficient for large candidate lists, as it loops through the whole candidate list, $X_c$, to find only one candidate to add. Moreover, many of the initial $n_d$ points will have to be replaced, requiring many loops if $n_d$ is moderately large. The adaptations we first describe are aimed at obtaining many exchanges per $X_c$ loop, to minimize the number of $X_c$ loops required. Every time a candidate is visited, we note the improvement in the criterion if it were added to the design. Hence, an approximation to the distribution of improvements can also be maintained. As we pass through the candidates, whenever a candidate's change is in the upper tail of this distribution, it is deemed "good" and considered for an exchange. (A similar process will be described below to search for a design point to complete the exchange.) Thus, each $X_c$ loop considers many "good" candidates for exchanges.

Figure 10:
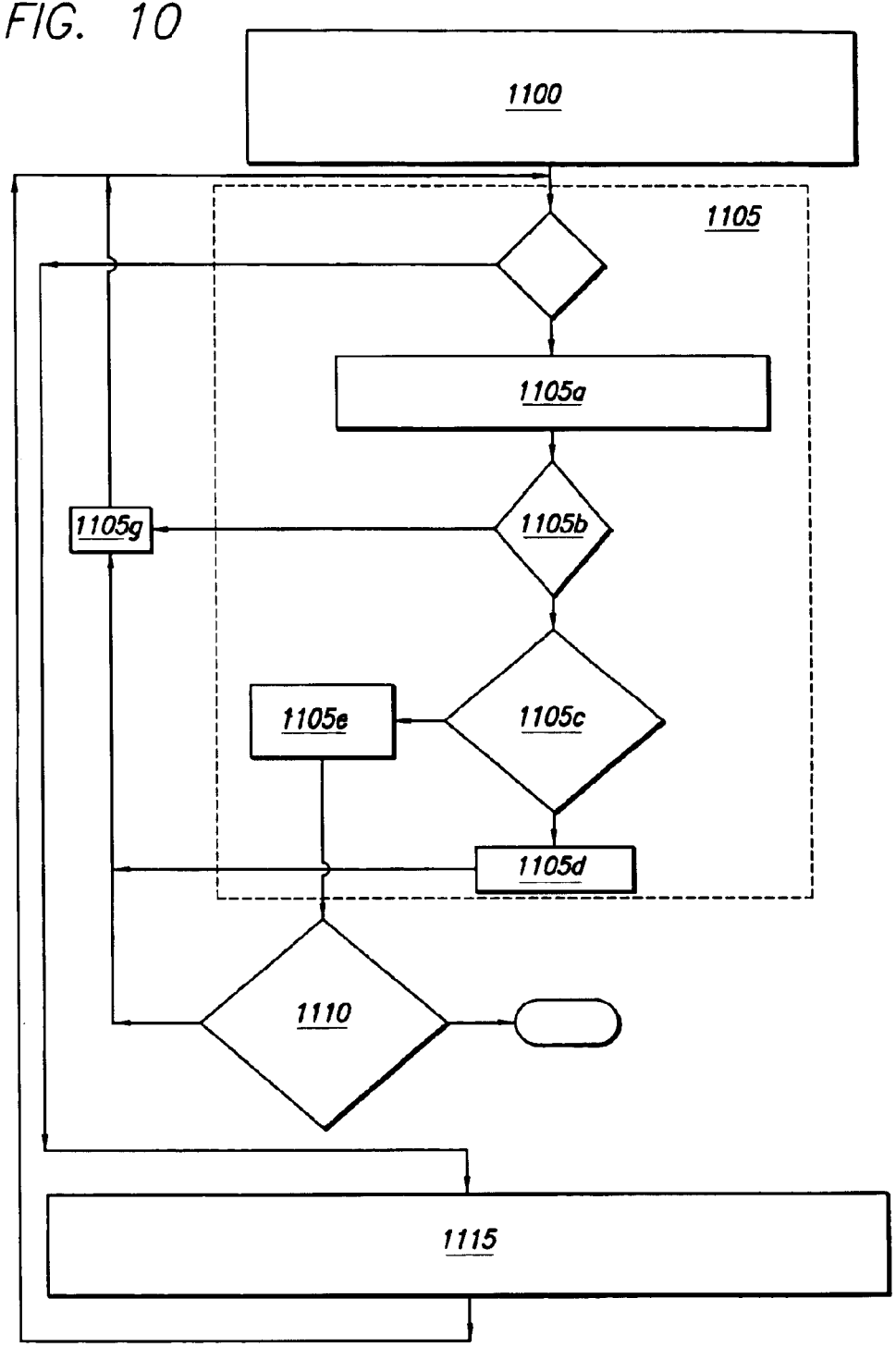
FIG. 10 is a flowchart illustrating a method of identifying "good" candidates, in accordance with an embodiment of the present invention.

Specifically, let $\delta_j$ denote the improvement (i.e., reduction) in the UCC criterion in Equation (8) if candidate j were added to the current $n_d$ design points to given $n_d+1$ points. The algorithm for identifying good candidates, with some explanation in parentheses, is as follows (and described with reference to FIG. 10):

1. (Step 1100 in FIG. 10) Initialization of the δ distribution. Randomly select a set of candidate points (e.g., 100 candidate points). Compute their δ values, and denote the sorted values by $\delta_{(1)} \geq \ldots \geq \delta_{(100)}$. Set $\lambda = n_d/N_c$ and $\delta^* = \delta_{(q)}$, where q=100 λ. (In Step 1105, if candidate j has $\delta_j \geq \delta^*$, it will be considered for an exchange. This rule will try approximately $n_d$ of the $N_c$ candidates during the first $X_c$ loop, because all $n_d$ initial design points may have to be replaced.)
2. (Step 1105) Loop through the candidates. For j=1, . . . , $N_c$ do the following steps:
   Compute $\delta_j$ and note the value for later use in updating δ* (Step 1105a).
   If $\delta_j \geq \delta^*$ (Step 1105b), then:
      Try exchanging candidate j with one of the current design points (Step 1105c)).
      If candidate j was exchanged, then
         Set $\delta_j = -100$. (As candidate j is now in the design, introducing it again is undesirable). (Step 1105d)
         Proceed to step 1105g (j=j+1) and being step 1105 again.
      else
         Replace δ* by δ*+10 λ(step 1105e). (A failed exchange suggests that δ* is allowing poor candidates to be considered, i.e., δ* is too small).
   If $\delta_j \geq \delta^*$ (Step 1105b) is not satisfied, then proceed to step 1105g and begin step 1105 again.

3. (Step 1110) Determine if there is any improvement in the complete loop. If there was no improvement in the criterion in the last $X_c$ loop, then stop. If there is any improvement in the complete loop, then proceed to step 1105g and begin step 1105 again.
4. (Step 1115) If j=$N_c$, then update $\delta^*$ for the next $X_c$ loop. Sort the $\delta_j$ values from the last $X_c$ loop and denote them by $\delta_{(1)} \geq \ldots \geq \delta_{(N_j)}$. Set $\lambda$ to half the previous value and $\delta^* = \delta_{(q)}$, where q=max(10, $N_c\lambda$). Go to Step 1105. (Decreasing $\lambda$ reduces the number of exchanges considered, because fewer exchanges are likely to improve the criterion with successive passes through the list. We always want to consider at least 10 promising candidates in the next $X_c$ loop, however, to be conservative about termination.)

Note that when a good candidate is found in Step 1105, we do not re-start the $X_c$ loop at the beginning. Rather we continue with the next candidate. These "floating" loops allow many exchanges in one $X_c$ loop.

Identifying Design Points for Exchange

Whenever a "good" candidate for inclusion in the design is identified by the rules in the above method, a design point must also be removed if an exchange is to take place. We evaluate the design points and identify a "bad" point, i.e., one that should be removed, using similar rules.

Figure 11:
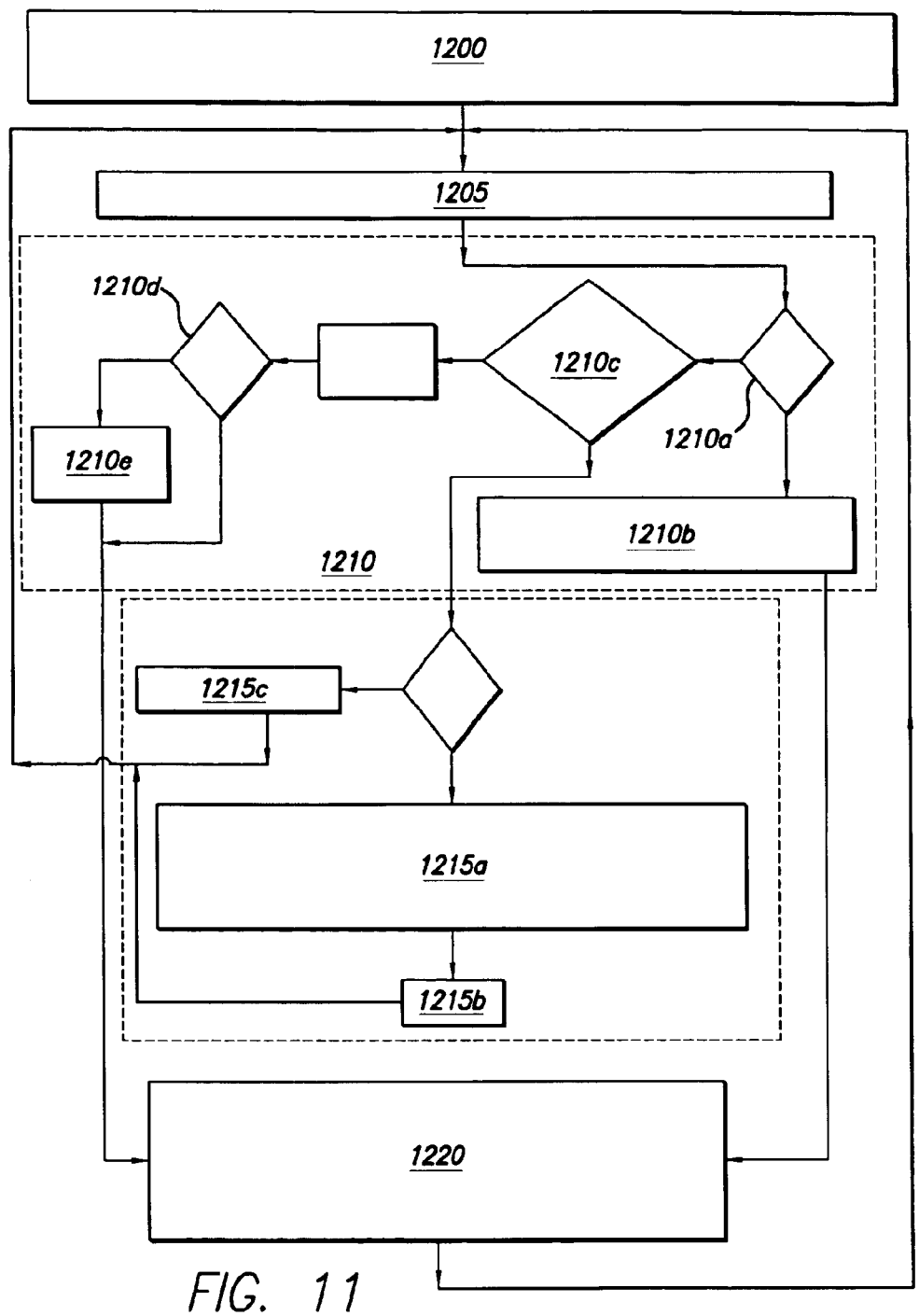
FIG. 11 is a flowchart illustrating a method of identifying design points for exchange, in accordance with an embodiment of the present invention.

For a fixed candidate j under consideration for inclusion, let $\Delta_i$ denote the overall improvement in the UCC criterion in Equation (8) if design point i of the $n_d$ current design points is replaced by candidate j. Thus, $\Delta_i$ includes the $\delta_j$ contribution from adding candidate j. A distribution of $\Delta_i$ values is maintained, and we implement an exchange as soon as a "good" $\Delta_i$ value is found, rather than search all $n_d$ design points. The details are as follows (and described with reference to FIG. 11):

1. (Step 1200 in FIG. 11) Initialization of the $\Delta$ distribution. If this is the first search of the design list, then:
    Randomly select a set of design points (e.g., 100 design points), compute their $\Delta$ values, and denote the sorted values by $\Delta_{(1)} \geq \ldots \geq \Delta_{(100)}$
    Set $\Delta^* = \Delta_{(q)}$, where q=100 $\lambda$, using the $\lambda$ value in effect for searching the candidate list (Exchanges with $\Delta_i \geq \Delta^*$ will be implemented.)
    Set i=1. (Start at the top of the design-point list.)
2. (Step 1205) Compute $\Delta_i$ and note the value for later use in updating $\Delta^*$.
3. (step 1210) If $\Delta_i \geq \Delta^*$ (see step 1201a), then
    Implement the exchange of design point i with candidate j (step 1210b). Proceed to step 1220.
    else if all design points have been tried (step 1210c), then
    Let $\Delta_{max}$ be the maximum $\Delta$ value over all the design points. If $\Delta_{max} \geq 0$ (step 1210d), then
        Implement the exchange of the design point giving $\Delta_{max}$ with candidate j. (Step 1210c). Proceed to step 1220.
        If $\Delta_{max} < 0$ (step 1201d), then proceed to step 1220.
    If all design points have not been tried (step 1210c), then proceed to step 1215.
4. (Step 1215) If i=$n_d$, then
    Update $\Delta^*$. Sort the $\Delta_i$ values from the last $X_d$ loop and denote them by $\Delta_{(1)} \geq \ldots \geq \Delta_{(n_d)}$. Set $\Delta^*$ =max(0.01, $\Delta_{(q)}$), where q=$n_d\lambda$, using the $\lambda$ value in effect for searching the candidate list. (Step 1215a).
    Set i=1 (Step 1215b); proceed to step 1205.
    else
    Set i to i+1 (step 1215c). Proceed to step 1205.
5. (Step 1220) If an exchange occurred in steps 1210b and 1210e or all design points had been tried in step 1210c, then
    Return to searching for the next "good" candidate to add. The next search for a "bad" design point to remove will start at Step 1205 with the current value of i.
    else
    Go to step 1205.

Note that in Step 1210, an exchange can occur with $\Delta_{max}=0$, i.e., it does not change the criterion. Allowing "neutral" exchanges of this type may be useful to break away from a design that is only locally optimal.

Updating the UCC Criterion

Finally, we describe how the criterion can be efficiently updated when only one point is changed, either when adding a candidate or when removing a design point.

When a point is added to or removed from the design, it will affect only one of the m cells in each subspace. Let $z_s$ be the number of design points in the affected cell in subspace s. If we are adding a point, then $z_s$ becomes $z_s+1$, and the change to $U_s$ in (5) is:

$$\{[(z_s+1)-1]^2 - (z_s-1)^2\} = (2z_s-1).$$

Note that $c_{si}(X_c)$ in equation (5) must equal 1, as a cell must be covered by at least one candidate if a point is to be added (or removed). Similarly, when a design point is removed, the change to $U_s$ in equation (5) is:

$$\{[(z_s-1)-1]^2 - (z_s-1)^2\} = (3-2z_s).$$

RESULTS

We now apply the above data-driven binning method and above fast design algorithm to select 729 molecules from the 29,217 NCI molecules.

Forming Cells

The distributions of the NCI molecules in 1-D (500) and 2-D (505) projections for all six descriptors are shown in FIG. 1. To apply the hybrid binning method described above, the first and last percentiles are assigned to EF bins, with EW bins between. There are six 1-D, fifteen 2-D, and twenty 3-D subspaces, and each of the 41 subspaces (1-D, 2-D, and 3-D) is divided into 729 cells. Over the 41 subspaces, on average there are 82.3% nonempty cells; the worst subspace X246 is with 63.8% nonempty cells.

Figure 5:
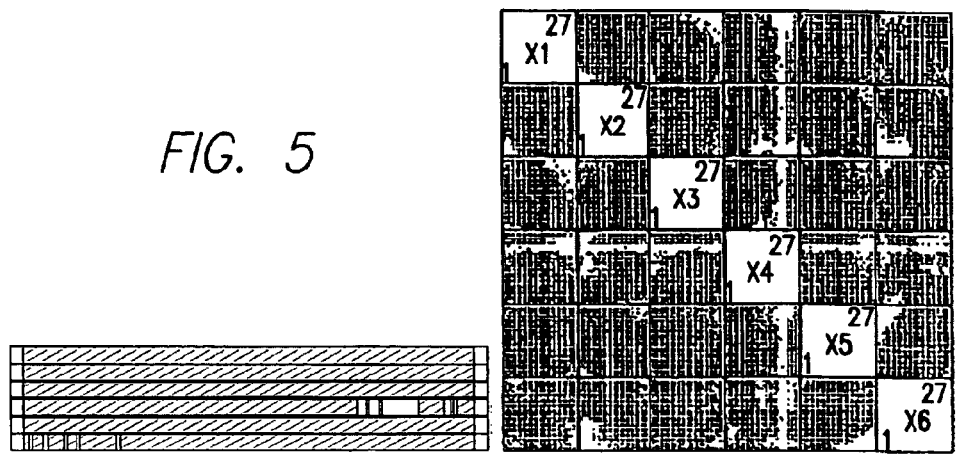
FIG. 5 illustrates diagrams of examples of plots of 1-D and 2-D non-empty cells for the NCI candidate points.

FIG. 5 shows the locations of the nonempty cells for all 1-D and 2-D subspaces. Inspection of the 1D plots reveals that adding a few extra EF bins to $x_4$ could further increase the proportion of nonempty cells in subspaces formed by $x_4$, but the current binning is acceptable and we do not pursue this.

UCC Design Versus Random Designs

Figure 6:
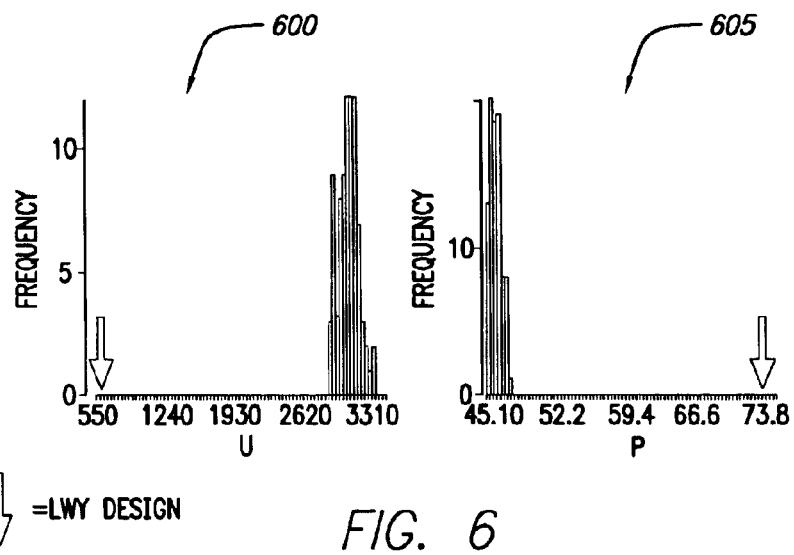
FIG. 6 illustrates charts comparing the UCC design to 100 random designs.

As a benchmark, we generate 100 random designs by randomly selecting 729 points from the 29,217 candidates. Their values of the average percentage coverage and uniform cell coverage criteria, P and U in Equations (4) and (8), respectively, are shown in FIG. 6. These random designs, on average, cover 45.6% of the cells occupied by the candidate points. The mean U value is 3108.1.

Starting from the first random design, our fast exchange algorithm described above, leads to an improved coverage. The arrows (600 and 605) in FIG. 6 show the resulting P and U values. Based on these criteria, the design made possible by the invention (UCC design) has much better 1-D, 2-D, and 3-D coverage than any of the 100 random designs. In terms of U (the smaller the better), the best random design has a value of 2905 compared with 591 (see arrow 600) for the UCC design. In terms of P (maximum 100%), the best random design has 47.1% coverage while the UCC design has 74.1% (see arrow 605).

Figure 7:
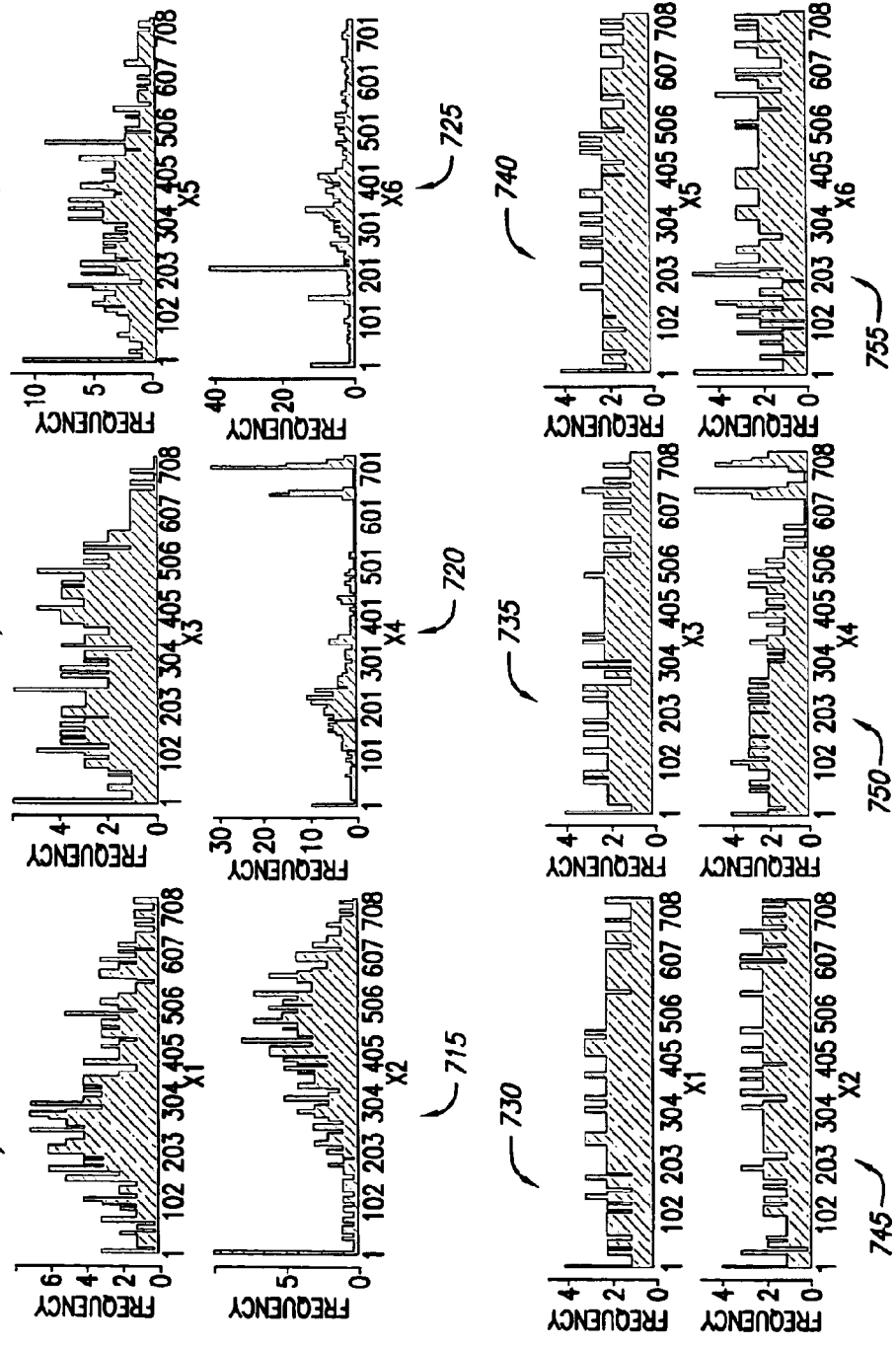
FIG. 7 illustrates plots of 1-D filled cells for the random and the UCC designs

FIG. 7 compares the cell frequencies in 1-D projections for the starting random design (first of the 100) (plots 700 to 705) and the UCC design (plots 730 to 755). Most of the cells for UCC design have one or two design points. The analogous 2-D projections of the design points are shown in FIG. 8, where a dot is plotted in a cell if there is at least one design point. (Plot 800 is the 2-D coverage for the random design, while plot 805 is the 2-D coverage for the UCC design). It is obvious from these figures that the UCC design has superior coverage in 1-D and 2-D projections. Similar plots for the 3-D projections show the same pattern.

UCC Design Versus Wynn's Algorithm

Table 1 compares the coverage and number of loops through the candidate set (proportional to computation time) for the UCC design algorithm with those for Wynn's original exchange algorithm (see, H. P. Wynn, "Results in the theory and construction of D-optimal experimental designs," Journal of the Royal Statistical Society B, 34, 133–147 (1972)). It is seen that the fast exchange algorithm produces better values of P and U. Although the UCC design algorithm makes more exchanges, it makes far fewer passes through the candidate and design points. In terms of computer CPU time, the UCC design algorithm took less than approximately one hour while Wynn's method took about 21 hours. These timings relate to implementations in SAS PROC IML on a Pentium II 400 MHz computer with 64 MB RAM. Faster speeds are undoubtedly possible by converting to, say, C++. To make it feasible to run Wynn's exchange algorithm, we incorporated the fast UCC update described above.

TABLE 1

Coverage and Running Time for a Random Design, the Wynn Exchange Algorithm, and the Fast Exchange Algorithm (UCC).

| Design Algorithm | No. of Exchanges | Coverage | | No. of loops | |
| --- | --- | --- | --- | --- | --- |
| | | U | P | $X_c$ | $X_d$ |
| Random | 0 | 2988.2 | 45.5 | 0.0 | 0.0 |
| Wynn | 759 | 605.3 | 74.1 | 759.0 | 759.0 |
| UCC | 1814 | 591.1 | 74.6 | 19.4 | 446.4 |

U = Uniform Cell Coverage and P = Average Percent Coverage (%).
One $X_c$ loop = 28488 visits to the candidate set and one $X_d$ loop = 729 visits to the design set.

The UCC algorithm makes most of the improvement in the first few loops through the candidates. Indeed, for the NCI database, it gave a better U value after five $X_c$ loops (less than about 16 minutes) than that of the final design from the Wynn algorithm. Similar results are obtained with Core98 molecules.

Our design problem is somewhat special for the following reasons. The candidate set of possible explanatory variable combinations is discrete, because only certain compounds can be made. Moreover, the set of discrete points can be large and highly irregular (see for example, FIG. 1). It is believed that two compounds must have very similar values of all critical descriptors to have similar properties. Thus, the design needs to cover the space densely. It is clearly impossible to achieve dense coverage in more than three dimensions at a time without an extraordinarily large design. Hence, we have proposed designs that aim for uniform coverage in all 1-D, 2-D, and 3-D projections.

The aim of such experimental designs is not just to discover highly active compounds, but to find several structurally different chemical classes. These provide options for further optimization of activity, physical properties, distribution, half-life, toxicity, etc. By covering the descriptor space uniformly, there is more chance of discovering multiple classes.

The design algorithm described above can efficiently deal with tens of thousands of compounds in the candidate set. Much larger sets of compounds will be of interest as technology advances. The algorithm may, for example, be also implemented with multiple processors.

Additional Results

It has been observed that careful selection of screening compounds using existing methods does not increase the hit rate over random selection (see, e.g., S. S. Young, Random Versus Rational—Which is Better for General Compound Screening? Network Science, www.netsci.org/science/screening/feature09.html (1996)). However, if active compounds are uniformly distributed in the descriptor space, which is arguably the case for a new assay, then, the uniform coverage design in accordance with the invention can lead to a higher hit rate than random selection which is expected to over sample compound dense regions. Here we are saying that one can get a higher hit rate because the active areas for a new assay are rather uniform although the compounds are not. Compounds are usually not uniformly distributed as they are made either because of ease of synthesis or following biological activity that will lead to dense clusters and gaps. For example, when a good compound for a particular assay is found, similar analogs are made where only a few of the selected atoms of the compound are changed.

If the active molecules are very evenly distributed over the molecular descriptor space, then the uniform coverage design in accordance with the invention has a better chance of selecting active molecules than a random selection. For example, suppose that there is one active molecule in each region in the space; some regions may have over 1000 molecules and some have few molecules. The UCC design has a better chance of selecting active molecules in the regions with few molecules.

So, does empiricism support this theory? Does selection of an initial screening set by the UCC design lead to a higher hit rate? To assess this we examined the hit rates for the 15 assays performed on the 23,056 Core98 compounds. The results show that the subsets gave slightly higher hit rates than random selection on 86% to 100% of the 14 assays. These positive results support the proposition that uniform coverage designs generate higher hit rates than random designs. These results are consistent with the proposition that regions of high potency are uniformly distributed through chemical space.

Our uniform coverage design algorithm selects diverse subsets of compounds for biological screenings. Using the UCC design algorithm, we selected a subset of 4096 compounds from 23056 Core98 compounds. We repeated the selection 5 times using different starting sets for the design selection. Each started with a different random selection. The biological activity ratings for 15 assays on the 23056 compounds were available from previous work. We examined the hit rates for the 15 assays on each of the 5 sets of 4096 compounds selected and noted the number of times the design gave a higher hit rate than a design selected at random. Random designs will approximate the hit rate for the entire sample so for our comparisons we use the hit rate for the entire sample.

The results are now described. For the 15 assays, the number of active compounds found (i.e., compounds with an activity value $\geq 50$) and the corresponding hit rates are summarized in Table 2. We will refer to these hit rates as the population or random hit rates. The hit rates for the 5 sets of compounds selected are also included in Table 2. The '?' columns next to the 'Hit rate' columns indicate whether the hit rate is higher (1) or not (0).

for the large candidate and design sizes we consider here, the Wynn algorithm would have taken weeks to months to find a (near) optimal design.
4. Classic designs typically exclude many objects because they use a mathematical model to infer what will happen in the regions without design points.
5. Classic space filling designs often have to remove outlying observations in an attempt to avoid having

TABLE 2

Population Hit Rates for 15 Assays on 23056 Compounds and the Corresponding Hit Rates for the 5 Designs.

| Var | | Population | | 5 Sets of 4096 compounds | | | | | | | | |
|---|---|---|---|---|---|---|---|---|---|---|---|---|
| | | Number | | UCC 1 | | UCC 2 | | UCC 3 | | UCC 4 | | UCC 5 | |
| Y | Assay | #Y2–50 | Hit rate | Hit rate | ? | Hit rate | ? | Hit rate | ? | Hit rate | ? | Hit rate | ? |
| y1 | assay1 | 46 | 0.200 | 0.317 | 1 | 0.293 | 1 | 0.317 | 1 | 0.293 | 1 | 0.289 | 1 |
| y2 | assay2 | 34 | 0.147 | 0.171 | 1 | 0.171 | 1 | 0.195 | 1 | 0.171 | 1 | 0.195 | 1 |
| y3 | assay3 | 35 | 0.145 | 0.171 | 1 | 0.024 | 0 | 0.146 | 1 | 0.073 | 0 | 0.098 | 0 |
| y4 | assay4 | 60 | 0.260 | 0.464 | 1 | 0.415 | 1 | 0.429 | 1 | 0.391 | 1 | 0.439 | 1 |
| y5 | assay5 | 53 | 0.230 | 0.342 | 1 | 0.317 | 1 | 0.391 | 1 | 0.342 | 1 | 0.391 | 1 |
| y6 | assay6 | 14 | 0.061 | 0.073 | 1 | 0.073 | 1 | 0.073 | 1 | 0.073 | 1 | 0.073 | 1 |
| y7 | assay7 | 14 | 0.061 | 0.122 | 1 | 0.122 | 1 | 0.122 | 1 | 0.122 | 1 | 0.122 | 1 |
| y8 | assay8 | 0 | 0.000 | | | | | | | | | | |
| y9 | assay9 | 13 | 0.056 | 0.122 | 1 | 0.122 | 1 | 0.122 | 1 | 0.122 | 1 | 0.122 | 1 |
| y10 | assay10 | 10 | 0.043 | 0.049 | 1 | 0.024 | 0 | 0.049 | 1 | 0.024 | 0 | 0.049 | 1 |
| y11 | assay11 | 103 | 0.447 | 0.906 | 1 | 0.806 | 1 | 0.732 | 1 | 0.757 | 1 | 0.830 | 1 |
| y12 | assay12 | 50 | 0.217 | 0.317 | 1 | 0.317 | 1 | 0.317 | 1 | 0.942 | 1 | 0.366 | 1 |
| y13 | assay13 | 507 | 2.199 | 2.930 | 1 | 2.856 | 1 | 2.905 | 1 | 2.881 | 1 | 2.956 | 1 |
| y14 | assay14 | 517 | 2.242 | 3.052 | 1 | 3.198 | 1 | 3.052 | 1 | 3.190 | 1 | 3.247 | 1 |
| y15 | assay15 | 10 | 0.043 | 0.049 | 1 | 0.049 | 1 | 0.049 | 1 | 0.049 | 1 | 0.073 | 1 |
| Number of times better | | | | | 14 | | 12 | | 14 | | 12 | | 13 |
| % out of 14 better | | | | | 100 | | 86 | | 100 | | 86 | | 93 |

For assay 8, all compounds had activity values less than 50. This assay is not useful for evaluating the hit rate. Of the remaining 14 assays, the UCC designs have higher hit rates than the hit rate of the entire sample (the expected hit rate of a random design) for 86 to 100% of the assays. The UCC designs consistently led to higher hit rates on 12 of the 14 assays. For Assays Y3 and Y10, the UCC designs yield both higher and lower hit rates.

Small, but consistent, increased hit rates for the UCC designs over random designs were observed. These positive results support the proposition that uniform coverage designs generate higher hit rates than random designs. These results are consistent with the proposition that regions of high potency are uniformly distributed through chemical space.

In summary, the differences between the system and method in accordance with various embodiments of the invention and the "classic" system and method are as follows:
1. Classic space filling designs keep track of the distances between all the design points or between each candidate point and its nearest design point. This becomes computationally expensive as the design gets large and if the number of candidate points is large.
2. Classic space filling designs attempt to fill all dimensions of the space.
3. Classic exchange algorithms typically search the entire candidate list to find the best point to exchange. They find one exchange point in one loop through the candidate set. The fast update feature significantly reduces the computation cost for measuring the coverage of a design when an exchange is made. Without this feature, many empty bins, or, if clustering is used, having many, very small clusters.
6. Classic designs typically have poor low dimensional coverage.

Application and Implementation of the UCC Algorithm

In a preferred embodiment, the method of the present invention is implemented on a digital computer. More specifically, the method is implemented in computer code that provides the necessary instructions for a processor performing the data manipulations necessary to run or execute the method. While the computer having memory and a processor is the preferred device in the invented system, other apparatus may also be used as is well-known by those skilled in the art.

Figure 12:
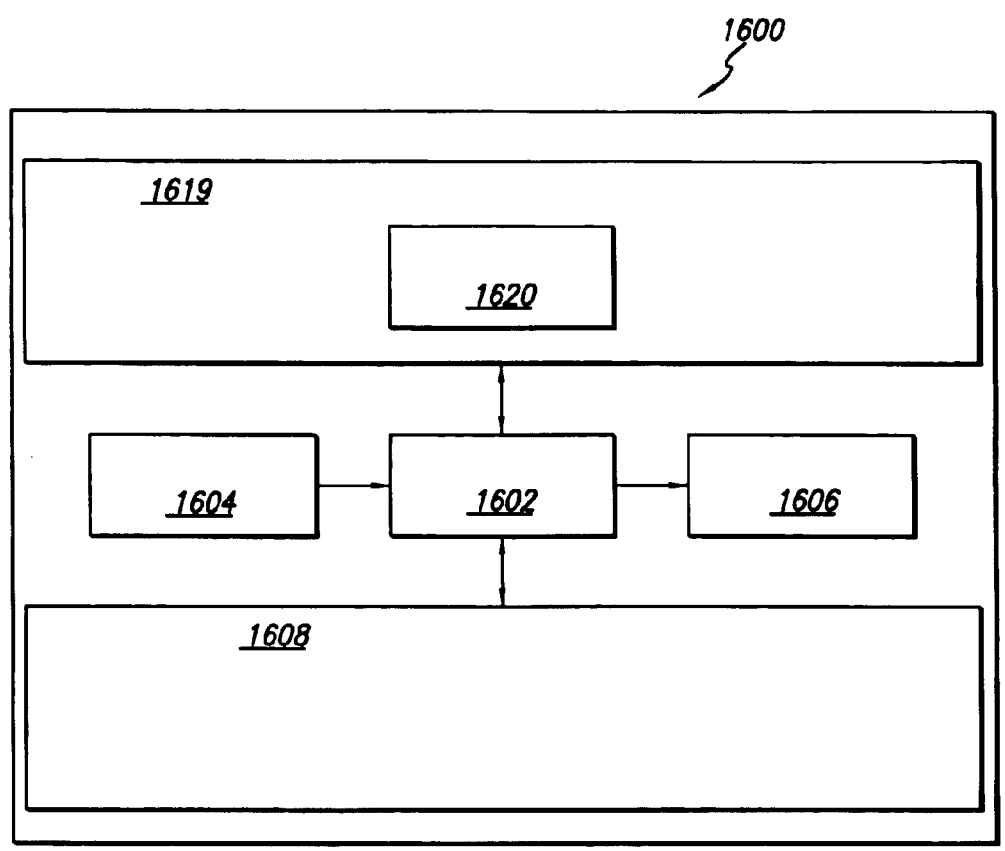
FIG. 12 illustrates a block diagram of a computer that can implement the present invention.

In one embodiment, the present invention is implemented on a computer 1600 as illustrated in FIG. 12. The computer 1600 comprises a central processing unit (CPU) 1602 for performing the calculations of the various methods described above, a storage device 1608 for storing data and files that can be retrieved by the processor 1602, an input device 1604 for enabling user interaction with the computer 1600, a display device 1606, and a memory 1619 for storing one or more programs during execution, such as a program that performs at least one of the above methods and/or a conventional program GUI OS 1620. Alternatively, the present invention may be implemented, for example, across a network of computers, enabling programs to be run by multiple processors at separate physical locations. Thus, a computer program was created that implemented the method and the software was installed on a computer.

It is also within the scope of the present invention to implement a program or code that can be stored in an electronically-readable medium to permit a computer to perform any of the methods described above.

Thus, while the present invention has been described herein with reference to particular embodiments thereof, a latitude of modification, various changes and substitutions are intended in the foregoing disclosure, and it will be appreciated that in some instances some features of the invention will be employed without a corresponding use of other features without departing from the scope of the invention as set forth.

What is claimed is:

1. A method of measuring uniformity of coverage of selected molecules, comprising:

measuring a lack of uniformity in each subspace wherein the lack of uniformity for 1-D subspaces is:

$$U_{1-D} = \frac{\sum_{i \in S_1} U_s}{|S_1|}$$

where $U_s$ is a measure of lack of uniformity is in subspace s, $U_s = \Sigma_i [n_{si}(X_d) - c_{si}(X_c)]^2$ and where design $X_d$ places $n_{si}(X_d)$ points in cell i of subspace s, $X_c$ is the candidate set, $c_{si}(X_c)=0$ if the candidate set $X_c$ does not cover cell i, $c_{si}(X_c)=1$ for cell i covered by candidate set $X_c$, $S_1$ is the set of all 1-D subspaces, and $|S_1|$ is the number of 1-D subspaces; and calculating an average of the lack of uniformity in each subspace.

2. The method of claim 1 where the lack of uniformity for 2-D subspace is:

$$U_{2-D} = \frac{\sum_{s \in S_2} U_s}{|S_2|}$$

where $S_2$ is the set of all 2-D subspaces, and $|S_2|$ is the number of 2-D subspaces.

3. The method of claim 2 wherein the lack of uniformity for 3-D subspace is:

$$U_{3-D} = \frac{\sum_{r \in S_2} U_s}{|S_3|}$$

where $S_3$ is the set of all 3-D subspaces, and $|S_3|$ is the number of 3-D subspaces.

4. The method of claim 3 wherein the weighted average of the lack of uniformity over all subspaces is:

$$U = \frac{(w_1 U_{1-D} + w_2 U_{2-D} + w_3 U_{3-D})}{w_1 + w_2 + w_3}$$

where $w_1$, $w_2$, and $w_3$ are weights.

5. An electronically-readably medium storing a program for permitting a computer to enable a method of measuring uniformity of coverage of selected molecules, comprising:

measuring a lack of uniformity in each subspace wherein the lack of uniformity for 1-D subspaces is:

$$U_{1-D} = \frac{\sum_{i \in S_2} U_s}{|S_1|}$$

where $U_s$ is a measure of lack of uniformity is in subspace s, $U_s = \Sigma_i [n_{si}(X_d) - c_{si}(X_c)]^2$ and where design $X_d$ places $n_{si}(X_d)$ points in cell i of subspace s, $X_c$ is the candidate set, $c_{si}(X_c)=0$ if the candidate set $X_c$ does not cover cell i, $c_{si}(X_c)=1$ for cell i covered by candidate set $X_c$, $S_1$ is the set of all 1-D subspaces, and $|S_1|$ is the number of 1-D subspaces; and calculating an average of the lack of uniformity in each subspace.

6. The electronically-readable medium storing a program for permitting a computer to enable a method of measuring uniformity of coverage of selected molecules in claim 5 where the lack of uniformity for 2-D $$U_{2-D} = \frac{\sum_{s \in S_2} U_s}{|S_2|}$$

subspace is:

where $S_2$ is the set of all 2-D subspaces, and $|S_2|$ is the number of 2-D subspaces.

7. The electronically-readable medium storing a program for permitting a computer to enable a method of measuring uniformity of coverage of selected molecules in claim 6 where the lack of uniformity for 3-D $$U_{3-D} = \frac{\sum_{s \in S_3} U_s}{|S_3|}$$

subspace is:

where $S_3$ is the set of all 3-D subspaces, and $|S_3|$ is the number of 3-D subspaces.

8. The electronically-readable medium storing a program for permitting a computer to enable a method of measuring uniformity of coverage of selected molecules in claim 7 wherein the weighted average of the lack of uniformity over all subspaces is:

$$U = \frac{(w_1 U_{1-D} + w_2 U_{2-D} + w_3 U_{3-D})}{w_1 + w_2 + w_3}$$

where $w_1$, $w_2$, and $w_3$ are weights.

9. A computer system for enabling a method of measuring uniformity of coverage of selected molecules, the computer system comprising:

a processor;

a memory coupled to the processor and storing therein a program executable by the processor for performing the steps of:

measuring a lack of uniformity in each subspace wherein the lack of uniformity for 1-D subspaces is:

$$U_{1-D} = \frac{\sum_{s \in S_2} U_s}{|S_1|}$$

where $U_s$ is a measure of lack of uniformity is in subspace s, $U_s = \Sigma_i [n_{si}(X_d) - c_{si}(X_c)]^2$ and where design $X_d$ places $n_{si}(X_d)$ points in cell i of subspace s, $X_c$ is the candidate set, $c_{si}(X_c)=0$ if the candidate set $X_c$ does not cover cell i, $c_{si}(X_c)=1$ for cell i covered by candidate set $X_c$, $S_1$ is the set of all 1-D subspaces, and $|S_1|$ is the number of 1-D subspaces; and calculating an average of the lack of uniformity in each subspace.

10. The computer system for enabling a method of measuring uniformity of coverage of selected molecules in claim 9 where the lack of uniformity for 2-D subspace is:

$$U_{2\text{-}D} = \frac{\sum_{s \in S_2} U_s}{|S_2|}$$

where $S_2$ is the set of all 2-D subspaces, and $|S_2|$ is the number of 2-D subspaces.

11. The computer system for enabling a method of measuring uniformity of coverage of selected molecules in claim 10 where the lack of uniformity for 3-D subspace is:

$$U_{3\text{-}D} = \frac{\sum_{s \in S_3} U_s}{|S_3|}$$

where $S_3$ is the set of all 3-D subspaces, and $|S_3|$ is the number of 3-D subspaces.

12. The computer system for enabling a method of measuring uniformity of coverage of selected molecules in claim 11 wherein the weighted average of the lack of uniformity over all subspaces is:

$$U = \frac{\left(w_1 U_{1\text{-}D} + w_2 U_{2\text{-}D} + w_3 U_{3\text{-}D}\right)}{w_1 + w_2 + w_3}$$

where $w_1$, $w_2$, and $w_3$ are weights.

13. The method in claim 1 wherein the steps are computer processed and distributed over multiple processors.

14. The method in claim 2 wherein the steps are computer processed and distributed over multiple processors.

15. The method in claim 3 wherein the steps are computer processed and distributed over multiple processors.

16. The method in claim 4 wherein the steps are computer processed and distributed over multiple processors.

* * * * *